United States Patent
Aso et al.

(10) Patent No.: US 6,489,536 B2
(45) Date of Patent: Dec. 3, 2002

(54) METHOD FOR PRODUCING CLONED BOVINES FROM CELLS OF A BOVINE INTRAMUSCULAR PREADIPOCYTE CELL LINE

(75) Inventors: Hisashi Aso, Tsukuba (JP); Norikazu Miyashita, Tsukuba (JP); Takato Takenouchi, Tsukuba (JP); Kyouhei Ozutsumi, Tsukuba (JP); Yasuo Shioya, Ryugasaki (JP); Tadayoshi Mitsuhashi, Tsukuba (JP); Norio Saito, Nishigo-mura (JP); Shuji Kobayashi, Nishigo-mura (JP); Kanako Kaneyama, Nishigo-mura (JP); Toshiyuki Kojima, Ushiku (JP); Shigeru Katamine, Nagasaki (JP)

(73) Assignees: Director General of National Agricultural Research Organization, Tsukuba (JP); President, National Livestock Breeding Center (NLBC) Independent Administrative Institution, Nishishirakawa-gun (JP)

( * ) Notice: Subject to any disclaimer, the term of this patent is extended or adjusted under 35 U.S.C. 154(b) by 0 days.

(21) Appl. No.: 09/907,944

(22) Filed: Jul. 19, 2001

(65) Prior Publication Data

US 2002/0129394 A1 Sep. 12, 2002

(30) Foreign Application Priority Data

Mar. 7, 2001 (JP) ......................................... 2001-063088

(51) Int. Cl.$^7$ ................................................ C12N 15/00
(52) U.S. Cl. ............................ 800/15; 800/14; 800/15; 435/325
(58) Field of Search ................................ 800/3, 18, 21, 800/22, 25; 435/455, 463, 320.1, 325

(56) References Cited

FOREIGN PATENT DOCUMENTS

| WO | WO 97/07668 | * | 3/1997 |
|---|---|---|---|
| WO | 97/07669 | | 3/1997 |
| WO | 98/30683 | | 7/1998 |
| WO | 01/00795 A1 | | 1/2001 |

OTHER PUBLICATIONS

FEhilly et.al.; Interspecific chimaerism between sheep and goat, 1984, Nature, vol. 307: 634–636.*
M. Sims, et al., "Production of Calves by Transfer of Nuclei from Cultured Inner Cell Mass Cells", Proc. Natl. Acad. Sci. USA, 91 (1994), pp. 6143–6147.
A. Colman, "Dolly, Polly and Other [Ollys]: Likely Impact of Cloning Technology on Biomedical Uses of Livestock", Genetic Analysis: Biomolecular Engineering, 15 (1997), pp. 167–173.
K.H.S. Campell, et al., "Nuclear Transfer From an Established Cell Line", Cell Biology: A Laboratory Handbook, Second Edition, vol. 3 (1998), pp. 487–501.
A.E. Schneike, et al., "Human Factor IX Transgenic Sheep Produced by Transfer of Nuclei from Transfected Fetal Fibroblasts", Science, vol. 278 (1997), pp. 2130–2133.
K.H.S. Campbell, et al., "Sheep Cloned by Nuclear Transfer from a Cultured Cell Line", Nature, vol. 380 (1996), pp. 64–66.

\* cited by examiner

*Primary Examiner*—Deborah Crouch
*Assistant Examiner*—Thaian N. Ton
(74) *Attorney, Agent, or Firm*—Oblon, Spivak, McClelland, Maier & Neustadt, P.C.

(57) ABSTRACT

For stably and efficiently producing cloned livestock, used is a uniform cultured cell strain as a donor cell for nuclear transplantation.

9 Claims, No Drawings

METHOD FOR PRODUCING CLONED BOVINES FROM CELLS OF A BOVINE INTRAMUSCULAR PREADIPOCYTE CELL LINE

FIELD OF THE INVENTION

The present invention relates to a method for producing livestock individuals from cells of an established cell line, precisely to a method for producing cloned livestock from cells of a uniform cultured cell strain (i.e. an established cell line) that serve as donor cells for nuclear transplantation. More precisely, the invention relates to a method for producing cloned cattle from cells of an established bovine intramuscular preadipocyte (hereinafter referred to BIP), a type of the uniform cultured cell strain for donor cells for nuclear transplantation.

BACKGROUND OF THE INVENTION

Heretofore, cloned livestock have been produced through nuclear transplantation of non-uniform somatic cells serving as donor cells. Concretely, cells, of which the origin is not clear, are sampled at random from ears or proligerous membranes (cumulus oophorus), and these are used for nuclear transplantation.

In thus method, however, it is extremely difficult to all the time efficiently produce cloned livestock even though the same experimental condition is repeated and continued.

In addition, even when the nucleus of a somatic cell is transplanted into an egg cell, it is impossible to accurately analyze the mechanism of its cleavage like that of fertilized eggs.

Heretofore, it has been recognized that fresh living cells are necessary for producing cloned livestock. For this, therefore, the general method is nuclear transplantation of somatic cells of specific livestock, as so mentioned hereinabove.

However, for all the time efficiently producing cloned livestock, it is necessary to culture cells of the same types applicable to cloned livestock production and to establish the cell line.

SUMMARY OF THE INVENTION

To solve the problems as above, we, the present inventors have assiduously studied a technique of culturing intramuscular fat cells of livestock, especially those of cattle, and a method of establishing the cell line, and, as a result, have succeeded in establishing a bovine intramuscular preadipocyte (BIP) usable for donor cells for nuclear transplantation. We have analyzed the established cell line as to whether or not it is suitable for donor cells for nuclear transplantation, and, as a result, have found that the BIP is useful for producing cloned cattle. On the basis of these findings, we have completed the present invention.

DETAILED DESCRIPTION OF THE INVENTION

Hereinafter, the present invention will be described in detail.

The present invention relates to a method for producing cloned livestock comprises using a cell of uniform cultured cell strain as a donor cell for nuclear transplantation. That is to say, in a method for producing cloned livestock, the improvement comprises using a cell of uniform cultured cell strain as a donor cell for nuclear transplantation.

More specifically, the present invention is shown as follows.

A method for producing cloned livestock, comprising;

a. preparing of recipient egg by taking cumulus oophorus-ovum complex out of ovaries; then maturing in vitro by cultivating it in a culture medium; separating and removing cumulus oophorus cells to obtain ovum; cutting a zona pellucida of the ovum; expelling a nucleus-containing cytoplasm to obtain enucleated cell b. transplanting a uniform cultured cell strain as a donor cell into a perivitelline space of the enucleated matured ovum c. transferring said ovum with the donor cell into a cell fusion medium, and then giving an electric shock whereby the donor cell is fused with the ovum to obtain nucleus-transplanted ovum d. culturing said nucleus-transplanted ovum to make it have a germinated blastocyst, and then selecting a good embryo e. transplanting the good embryo into a surrogate livestock, and f. checking whether said embryo get pregnant, and further monitoring the condition of fetus.

Following are embodiments of the present invention.

The method as claimed above, wherein the livestock is a livestock selected from the group consisting of cattle, sheep, goats and pigs.

The method as claimed above, wherein the cell of uniform cultured cell strain is a BIP.

The method as claimed above, wherein a cryopreserved cell is utilized as the bovine intramuscular preadipocyte.

In the method of the invention, BIP can be preferably used as the uniform cultured cell strain. The livestock to which the method of the invention is applicable include, for example, cattle, sheep, goats and pigs. Of those, especially preferred are cattle.

BIP can be established as follows: Fat cells and preadipocytes (fat precursor cells) are separated from bovine musculi longissimus thoracis with marbling (fat tissue) therein, and these are cultured for primary culture. Concretely, the marbling part is collected from the musculi longissimus thoracis of a slaughtered cow, and the fat tissue is separated from it. The fat tissue is analyzed for the presence or absence of cell growth therein, and the growth is only observed in the preadipocytes. The fat tissue is treated with enzyme to collect the preadipocyte.

Next, the preadipocytes are sub-cultured and cloned according to an ordinary method, and a single BIP cell line having the ability to grow is thereby established.

The cells of the BIP cell line are analyzed, and it is found that they are particular cells of pericytes existing around blood vessels. Up to the present, no one has succeeded in establishing the cell line of the pericytes.

One embodiment of the invention is described below, which is for producing cloned livestock from BIP serving as donor cell for nuclear transplantation.

The method of producing cloned livestock may be basically the same as the conventional method of producing them from somatic cell serving as donor cell. Concretely, a cumulus oophorus-ovum complex (COCs) is taken out of the ovary of a slaughtered cow, and this is matured in vitro. The cumulus oophorus cells are separated and removed from the COCs, and the nucleus is removed from the resulting ovum. BIP cell is transplanted into enucleated ovum, and these are fused with an electric pulse imparted thereto to make a nucleus-transplanted ovum.

Next, the nucleus-transplanted ovum is cultured to generate a blastocyst. From those, good embryos are selected, and each is transplanted in a surrogate cow. The surrogate cows with the embryos transplanted are checked as to they get pregnant or not. While the condition of the fetus therein is monitored, each surrogate cow is raised, and the birth of a cloned calf from it is waited for.

Since the BIP cells are of a cloned uniform cell line, their properties are stable, and all generations of the cells can be used for nuclear transplantation. Concretely, the present inventors' experiments have shown that the cells can be sub-cultured up to at least 60 generations with no chromosomal aberrations in at least these 60 generations of the sub-cultured cells, and that there is no change of the rate of blastocyst generation in the nuclear transplantation of the sub-cultured cells.

The BIP cells can be cryopreserved for storage in any known manner. The cryopreserved cells can be thawed anytime before use. In addition, the BIP cells can easily undergo any desired gene introduction or deletion. Therefore, for example, it is possible to produce cattle that are not infected with bovine spongiform encephalopathy (BSE).

According to the invention, cloned livestock can be stably and efficiently produced. In addition, since the donor cells used in the invention are of a uniform cultured cell strain, they can be cryopreserved, and can be thawed before use. Therefore, the same donor cells can be cultured anytime when necessary. Moreover, specific genes can be easily introduced into or deleted from the donor cells through a technique of genetic engineering, and, in addition, it is possible to confirm the gene introduction or deletion after the genetic modification.

EXAMPLE

The invention is described in more detail with reference to the following Examples, which, however, are not intended to restrict the scope of the invention.

Experimental Test 1

Establishment of BIP Cell Line

Fat cells and preadipocytes were separated from bovine musculi longissimus thoracis with marbling (fat tissue) therein, and these were cultured for primary culture. Concretely, the marbling part was collected from the musculi longissimus thoracis of a slaughtered cow of Japanese Black Cattle, and the fat tissue was separated from it and then treated with an enzyme. This was then centrifuged to separate the fat cells and the preadipocytes.

The thus-collected cells were cultured in a 10% fetal calf serum-added D-MEM culture medium put in a collagen-coated plastic laboratory dish. After 5 or 7 days, these were recovered and their number was counted. From the data, the rate of cell growth from the start of the cell culture was calculated, and only the preadipocytes were found to have grown.

Consequently, insulin (50 ng/ml), dexamethasone (0.25 $\mu$M), acetic acid (10 mM), biotin (33 $\mu$M), pantothenate (17 $\mu$M), ascorbate (100 $\mu$M) and octanoate were added to the culture medium to prepare a medium for inducing differentiation, in which the preadipocytes were cultured. The fat drops and the triglyceride having accumulated in the cells were quantitatively determined. From the data, obtained was the degree of differentiation of the preadipocytes into fat cells (this means the differentiation ability of the preadipocytes).

From the preadipocytes having grown as above, obtained was a single cell strain according to a limiting dilution-culture method. Based on the data of the growth rate and the differentiation rate of the preadipocytes of the single cell strain, the cell line of the BIP cells was established.

The BIP cells were cultured in a culture medium containing 0.1 $\mu$g/ml of colcemid, at 37° C. for 2 hours. Next, the culture was transferred into a centrifugal precipitation tube, and the cells were washed with a physiological saline solution. The wash waste was also put into the centrifugal precipitation tube. Using a trypsin-EDTA solution, the cells were detached, then suspended in the medium in the centrifugal precipitation tube, and returned to the centrifugal precipitation tube. The contents of the tube were centrifuged, the supernatant was removed, and the cells in the tube were made to float therein, to which was added 0.075 M potassium chloride. Gently pipetted, this was then kept warmed at 37° C. for 20 minutes.

Next, a fixative solution (methanol/glacial acetic acid=3/1) was added directly to this, and then gently and slowly mixed. This was centrifuged, and the supernatant was removed. The fixative solution was again added thereto. This process was repeated two times. After the supernatant was finally removed, the cells were suspended in the fixative solution to float therein. One drop of the resulting suspension was put down on a glass slide that had been in a container kept at −30° C., and then dried in air.

The thus-dried glass slide was left at a room temperature for a few days, then dipped in a trypsin solution at 4° C. and treated with it for 30 seconds to 2 minutes. Next, the glass slide was dipped in ethanol to stop the trypsin reaction. After washed with distilled water, this was stained with a Giemsa solution for 10 minutes. Then, this was washed with water, dried in air and then sealed up.

The thus-formed glass slide was observed with a microscope, and the number of the chromosomes seen on it was counted.

As a result, no chromosomal aberrations were found in the 60 bovine chromosomes of the BIP cells having been sub-cultured up to 60 generations.

Example 1

1) Preparation of Recipient Egg

Ovaries were collected in a slaughterhouse. These were put into a physiological saline solution at 25° C., and carried to the inventors' laboratory. The cumulus oophorus-ovum complex (COCs) was taken out of the ovaries, and matured in vitro by cultivating it in a 5% bovine serum-containing TCM199 medium for 20 hours.

The matured COCs was treated in a 0.5% hyaluronidase-containing M2 medium for 5 minutes, and the cumulus oophorus cells were separated and removed from it through gentle pipetting. Next, in a physiological saline solution containing 20% bovine serum and 5 $\mu$g/ml cytochalasin B, the zona pellucida of the ovum (this is a denuded metaphase II oocyte) was cut in the vicinity of the polar body. With that, the nucleus-containing cytoplasm was expelled from the cell using a glass needle to thereby enucleate the cell. The enucleation was confirmed by staining the cell with a fluorescent reagent (Hoechst's 33342).

2) Nuclear Transplantation

Using a glass pipette for microinjection, one BIP cell obtained in Experimental Test 1 and serving as a donor cell was transplanted into the enucleated matured ovum, precisely into the perivitelline space and adjacent to the yolk of the ovum.

The ovum with the donor cell transplanted thereinto was transferred into a Zimmerman cell fusion medium. With needle-type electrodes connected thereto, this was given an electric shock two times at 25 V for 10 $\mu$seconds, whereby the donor cell was fused with the ovum. After the cell fusion, the nucleus-transplanted ovum was treated with a 5 μM calcium ionophore for 5 minutes.

Next, the nucleus-transplanted ovum was cultured in a TCM199 medium containing 5% bovine serum and 10 μg/ml cycloheximide, for 6 hours, and then in a 5% bovine serum-containing CR1aa medium for 8 days.

The rate of cell fusion in nuclear transplantation was 86/161 (53.4%), and the initial incidence of cell fusion was 85/86 (98.8%). Finally, the rate of blastocyst generation was 53/86 (61.6%). The BIP cell-derived nucleus-transplanted embryos were ranked, and good ones were selected from them. The thus-selected embryos were separately transplanted into 16 surrogate cows, Holsteins.

3) Process After Transplantation into Surrogate Cows

The embryo-transplanted Holsteins were checked through echography as to they got pregnant or not, and 5 of these 16 Holsteins were found to have gotten pregnant. In this stage, the embryos in these pregnant Holsteins were all good, and their heart beats were confirmed.

Finally, one of the five pregnant Holstain born a normal he-calf (of Japanese Black Cattle, having a body weight at birth of 37 kg). Of the other four, two aborted, one had a stillbirth on its delivery; and another one had a stillbirth owing to its accidental death.

4) DNA Analysis

DNA was extracted from the donor cell (BIP cell) and from the leukocyte of the born, cloned calf. 23 sets of primers were designed, based on the sequence just outside the bovine polymorphic microsatellite region, and these primers were labeled with any of fluorescent dyes, 6-FAM, HBX and TET.

To 0.4 μM of each of the these fluorescent primers, added were 20 ng of DNA, 1.7 mM of $MgCl_2$, 10 mM of Tris-HCl (pH 8.3), 50 mM of KCl, 200 μM of dNTPs, and 50 units/ml of Taq DNA polymerase to be 15 μl in total.

Using a thermal cycler, the mixture was subjected to 29 cycles of PCR at 94° C. for 20 seconds each. The PCR product was separated through electrophoresis in a sequencer, Perkin-Elmer 373A Model, and the resulting band pattern was analyzed by the use of Genescan 672™ and Genotyper™ (both from Perkin-Elmer) (reference: Inoue, M. et al., Individual Identification and Paternity Control of Japanese Black Cattle based on Microsatellite Polymorphism, Anim. Sci. Technol., 68, 443–449, 1997). As a result, the band pattern of the DNA from the BIP cell corresponded to that of the DNA from the cloned calf. This supports that the born calf is a BIP cell-derived cloned calf.

While the invention has been described in detail and with reference to specific embodiments thereof, it will be apparent to one skilled in the art that various changes and modifications can be made therein without departing from the spirit and scope thereof.

What is claimed is:

1. A method for producing cloned bovine livestock comprising:

transferring a nucleus from a bovine intramuscular preadipocyte cultured cell into an enucleated bovine oocyte to obtain a nucleus-transplanted ovum;

activating the nucleus-transplanted ovum under conditions suitable for embryo formation;

transferring the embryo to a surrogate bovine female; and developing said bovine livestock to term.

2. The method of claim 1, wherein said bovine intramuscular preadipocyte is obtained from a uniform cultured cell line.

3. The method of claim 1, wherein said bovine intramuscular preadipocyte is a cryopreserved cell that has been thawed.

4. The method of claim 1, comprising transferring the nucleus from a bovine intramuscular preadipocyte into a bovine oocyte.

5. The method of claim 1, wherein said bovine intramuscular preadipocyte cultured cell is obtained from a Japanese Black cow.

6. The method of claim 1, wherein said surrogate bovine female is a Holstein.

7. The method of claim 1, wherein said enucleated oocyte is produced by cutting the zona pellucida of an ovum and expelling the nucleus-containing cytoplasm, thereby obtaining an enucleated oocyte.

8. The method of claim 1, wherein said bovine intramuscular preadipocyte and said ovum are fused by electric shock to produce a nucleus-transplanted ovum.

9. The method of claim 1, further comprising adding or deleting one or more gene(s) from said bovine intramuscular preadipocyte.

* * * * *